United States Patent [19]
Cheung et al.

[11] Patent Number: 5,587,288
[45] Date of Patent: Dec. 24, 1996

US005587288A

[54] REGULATION OF EXOPROTEIN IN STAPHYLOCOCCUS AUREUS

[75] Inventors: Ambrose Cheung, New York; Vincent A. Fischetti, West Hempstead, both of N.Y.

[73] Assignee: The Rockefeller University, New York, N.Y.

[21] Appl. No.: 248,505

[22] Filed: May 24, 1994

[51] Int. Cl.$^6$ .............................. C12Q 1/68; C07K 13/00; C07H 21/02; C07H 21/04
[52] U.S. Cl. .............................. 435/6; 530/350; 536/23.1; 536/24.3
[58] Field of Search ................................ 435/6; 530/350; 536/23.1, 24.3

[56] References Cited

PUBLICATIONS

Cheung, et al, "Regulation of Exoprotein Expression by Staphlococcus Aureus by a locus (SAR) distinct from Agr", Jul. 1992, PNAS 89:6462–6466.

Camilli, et al "Insertional Mutagenesis of Listeria monocytogenes with a Novel Tn917 Derivative That Allows Direct Cloning of DNA Flanking Transposon Insertions", Jul. 1990, J. Bacteriology 172:3738–3744.

Cheung et al "Cloning and Sequencing of sarA of Staphylococcus aureus, a Gene required for the Expression of agr", Jul. 1994, J. Bacteriology 176:4168–4172.

McConkey "Human Genetics: The Molecular Revolution" 1993, Jones and Bartlett Publishers, Boston, p. 33.

Sambrook et al, Molecular Cloning–A Laboratory Manual, CSH Press, Cold Spring Harbor, New York, 1989, pp. 17.2–17.44.

Wnendt et al, "Characterization of the gene encoding α–sarcin, a ribosome–inactivating protein secreted by *Aspergillus giganteus*" (Mar. 1993), Gene 124:239–244.

Nandivada et al, "SAR–2: Identification of a novel plasmid–encoded β-lactamase from India", 1989, Fems Microbiol. Lett. 57: 219–222.

Lawton, et al, "Acquired Resistance Signal Transduction in Arabidopsis is Ethylene Independent", 1994, Plant Cell 6:581–588.

*Primary Examiner*—W. Gary Jones
*Assistant Examiner*—Jeffrey Fredman
*Attorney, Agent, or Firm*—Burns, Doane, Swecker & Mathis, L.L.P.

[57] ABSTRACT

This invention relates to the recognition and control of bacterial infections, particularly infections caused by *Staphylococcus aureus* (*S. aureus*). The present invention provides the staphylococcal accessory regulatory (sar) protein, and the gene encoding the sar protein (sar). The present invention also provides a diagnostic method for determining the pathogenicity of an *S. aureus* isolate using the sar gene.

3 Claims, 2 Drawing Sheets

Fig. 2

```
1    AATAGGGAGGTTTTAAACATGGCAATTACAAAAATCAATGATTGCTTTGAGTTGTTATCA  60
                      METAlaIleThrLysIleAsnAspCysPheGluLeuLeuSer

ATGGTCACTTATGCTGACAAATTAAAAAGTTTAATTAAAAAGGAATTTTCAATTAGCTTT  120
15   METValThrTyrAlaAspLysLeuLysSerLeuIleLysLysGluPheSerIleSerPhe

GAAGAATTCGCTGTATTGACATACATCAGCGAAAACAAAGAGAAAGAATACTATCTTAAA  180
35   GluGluPheAlaValLeuThrTyrIleSerGluAsnLysGluLysGluTyrTyrLeuLys

GATATTATTAATCATTTAAACTACAAACAACCACAAGTTGTTAAAGCAGTTAAAATTTTA  240
55   AspIleIleAsnHisLeuAsnTyrLysGlnProGlnValValLysAlaValLysIleLeu

TCTCAAGAAGATTACTTCGATAAAAAACGTAATGAGCATGATGAAAGAACTGTATTAATT  300
75   SerGlnGluAspTyrPheAspLysLysArgAsnGluHisAspGluArgThrValLeuIle

CTTGTTAATGCACAACAACGTAAAAAAATCGAATCATTATTGAGTCGAGTAAATAAACGA  360
95   LeuValAsnAlaGlnGlnArgLysLysIleGluSerLeuLeuSerArgValAsnLysArg

ATCACTGAAGCAAACAACGAAATTGAACTATAA
115  IleThrGluAlaAsnAsnGluIleGluLeu---
```

| SarA | 17  | TYADKLKSLIKKEFSISFEEFAV         | 39  |
|------|-----|---------------------------------|-----|
|      |     | +Y+++ + L KK F +S EE ++         |     |
| VirF | 93  | SYSEEKRGLNKKIFLLSEEEVSI         | 115 |
| SarA | 43  | ISENKEKEYYLKDIINHLNYKQPQVVKAVK  | 72  |
|      |     | + +N EK + L DI N+LN  +  V K ++  |     |
| VirF | 167 | VEKNIEKRWRLSDISNNLNLSEIAVRKRLE  | 19  |

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:

( A ) LENGTH: 393 base pairs

5,587,288

-continued ( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 19..390

( x i ) SEQUENCE DESCRIPTION: SEQ ID NO:1:

```
AATAGGGAGG TTTTAAAC ATG GCA ATT ACA AAA ATC AAT GAT TGC TTT GAG          51
                    Met Ala Ile Thr Lys Ile Asn Asp Cys Phe Glu
                     1           5                   10

TTG TTA TCA ATG GTC ACT TAT GCT GAC AAA TTA AAA AGT TTA ATT AAA          99
Leu Leu Ser Met Val Thr Tyr Ala Asp Lys Leu Lys Ser Leu Ile Lys
             15                  20                  25

AAG GAA TTT TCA ATT AGC TTT GAA GAA TTC GCT GTA TTG ACA TAC ATC         147
Lys Glu Phe Ser Ile Ser Phe Glu Glu Phe Ala Val Leu Thr Tyr Ile
         30                  35                  40

AGC GAA AAC AAA GAG AAA GAA TAC TAT CTT AAA GAT ATT ATT AAT CAT         195
Ser Glu Asn Lys Glu Lys Glu Tyr Tyr Leu Lys Asp Ile Ile Asn His
         45                  50                  55

TTA AAC TAC AAA CAA CCA CAA GTT GTT AAA GCA GTT AAA ATT TTA TCT         243
Leu Asn Tyr Lys Gln Pro Gln Val Val Lys Ala Val Lys Ile Leu Ser
 60                  65                  70                  75

CAA GAA GAT TAC TTC GAT AAA AAA CGT AAT GAG CAT GAT GAA AGA ACT         291
Gln Glu Asp Tyr Phe Asp Lys Lys Arg Asn Glu His Asp Glu Arg Thr
                 80                  85                  90

GTA TTA ATT CTT GTT AAT GCA CAA CAA CGT AAA AAA ATC GAA TCA TTA         339
Val Leu Ile Leu Val Asn Ala Gln Gln Arg Lys Lys Ile Glu Ser Leu
             95                 100                 105

TTG AGT CGA GTA AAT AAA CGA ATC ACT GAA GCA AAC AAC GAA ATT GAA         387
Leu Ser Arg Val Asn Lys Arg Ile Thr Glu Ala Asn Asn Glu Ile Glu
         110                 115                 120

CTA TAA                                                                  393
Leu
```

( 2 ) INFORMATION FOR SEQ ID NO:2:

( i ) SEQUENCE CHARACTERISTICS:
( A ) LENGTH: 23 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:2:

```
Thr Tyr Ala Asp Lys Leu Lys Ser Leu Ile Lys Lys Glu Phe Ser Ile
 1               5                  10                  15

Ser Phe Glu Glu Phe Ala Val
                 20
```

( 2 ) INFORMATION FOR SEQ ID NO:3:

( i ) SEQUENCE CHARACTERISTICS:
( A ) LENGTH: 23 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:3:

```
Ser Tyr Ser Glu Glu Lys Arg Gly Leu Asn Lys Lys Ile Phe Leu Leu
```

```
                1                       5                              1 0                             1 5

Ser   Glu   Glu   Glu   Val   Ser   Ile
                            2 0
```

( 2 ) INFORMATION FOR SEQ ID NO:4:

( i ) SEQUENCE CHARACTERISTICS:
         ( A ) LENGTH: 30 amino acids
         ( B ) TYPE: amino acid
         ( C ) STRANDEDNESS: single
         ( D ) TOPOLOGY: linear ( i i ) MOLECULE TYPE: protein ( x i ) SEQUENCE DESCRIPTION: SEQ ID NO:4:

```
   Ile   Ser   Glu   Asn   Lys   Glu   Lys   Glu   Tyr   Tyr   Leu   Lys   Asp   Ile   Ile   Asn
   1                       5                             1 0                            1 5

His   Leu   Asn   Tyr   Lys   Gln   Pro   Gln   Val   Val   Lys   Ala   Val   Lys
                     2 0                              2 5                      3 0
```

( 2 ) INFORMATION FOR SEQ ID NO:5:

( i ) SEQUENCE CHARACTERISTICS:
         ( A ) LENGTH: 30 amino acids
         ( B ) TYPE: amino acid
         ( C ) STRANDEDNESS: single
         ( D ) TOPOLOGY: linear ( i i ) MOLECULE TYPE: protein ( x i ) SEQUENCE DESCRIPTION: SEQ ID NO:5:

```
   Val   Glu   Lys   Asn   Ile   Glu   Lys   Arg   Trp   Arg   Leu   Ser   Asp   Ile   Ser   Asn
   1                       5                             1 0                            1 5

Asn   Leu   Asn   Leu   Ser   Glu   Ile   Ala   Val   Arg   Lys   Arg   Leu   Glu
                     2 0                              2 5                      3 0
```

REGULATION OF EXOPROTEIN IN *STAPHYLOCOCCUS AUREUS*

FIELD OF THE INVENTION

This invention relates to the recognition and control of bacterial infections, particularly infections caused by *Staphylococcus aureus* (*S. aureus*).

BACKGROUND OF THE INVENTION

*S. aureus* is a major human pathogen that has the ability to produce a variety of extracellular and cell-wall associated proteins many of which are involved in pathogenesis (6). In vitro, most of these exoproteins are usually synthesized and secreted in the postexponential phase (6). However, synthesis of a number of surface-associated proteins that clearly play a role in infection is repressed postexponentially (6,11).

In S. aureus, the postexponential phase regulation of virulence determinants and other exoprotein genes involves at least three global regulatory systems, agr, xpr, and sar (3,11,20). Most of the exoprotein regulated by agr are either not synthesized or synthesized at a reduced rate in agr mutants while the synthesis of surface proteins is upregulated (11). The aqr locus has been cloned (11) and consists of at least five genes, agrA, agrB, agrC, agrD and the hld (δhemolysin) gene. Sequence analysis indicated that it has features suggestive of a two component regulatory system as described in other procaryotes (11). In particular, the argB is the signaling component while agrA corresponds to the transcription activation element (11,14). The agr locus is composed of two divergent transcription units designated RNAII (agr A,B,C and D genes) and RNAIII (hld gene). Mutations in either agrA or agrB has led to decreased transcription of RNAIII (11,16). RNAIII, which also encodes the 26 residue hemolysin polypeptide, is essential for the transcriptional control of exoprotein synthesis (e.g., α hemolysin) (11).

A second locus, termed xpr, was recently identified by TnSSI insertion into the staphylococcal chromosome. Northern blot studies indicated that the xpr locus regulates exoprotein synthesis at the mRNA level (9). Interestingly, both xpr and agr mutants produced greatly reduced amount of hemolysin. This finding together with the observation that the RNAIII level is decreased in a xpr mutant suggest that the xpr and agr loci may behave as interactive regulatory genes (9,20).

An additional locus in *S. aureus*, designated sar, that is involved in the regulation of exoproteins has been reported (3). Inactivation of this locus by Tn917LTV1 insertion has resulted in decreased expression of several extracellular (e.g., β-hemolysin) and cell wall proteins (3). Phenotypic, Southern blot and genetic mapping analyses indicated that this locus is distinct from aqr and xpr (3,4). Using the DNA sequence flanking the Tn917LTV1 insertion as a probe, the sar gene that is involved in the regulation of exoprotein synthesis has been cloned and sequenced. Additional transcriptional and phenotypic studies revealed that this sar gene is necessary for the optimal expression of agr.

Inactivation of the sar locus has resulted in alterations of expression of exoproteins in three different *S. aureus* isolates (strains DB, RN6390 and RN450) (3,4). Using both α and β hemolysin genes as probes, transcriptional studies of strains with well-defined genetic backgrounds (i.e., RN6390 and RN450) revealed that the sar locus probably regulates exoprotein genes positively at the mRNA level (4). The regulation of exoprotein genes (e.g., α and β hemolysins) by the sar locus in vitro was found to begin at midlog phase and continued onto the postexponential phase (4). This mode of regulation is similar to that of agr on target exoprotein gene transcription.

To elucidate the interaction between the sar and agr loci, the level of the RNAIII transcript in sar mutants as well as mutants complemented was assayed with an intact sarA gene. The data suggested that the levels of RNAIII were related to a functional sarA gene (FIG. 1). It was also found possible to overcome the deficiency in β and δ hemolysin expression in a sar mutant by introducing a plasmid carrying RNAIII under the control of a promoter uninfluenced by sar. To rule out the possibility of some concerted interaction, Northern blot analysis was employed to determine that the level of sar mRNA did not appear to be altered appreciably in an agr background (RN6911) (11) as compared to the wild type parent RN6390. Taken together, these data suggest that the agr locus is under the control of sar.

Analysis of the sarA gene sequence leads to several interesting observations. First, there is no helix-turn-helix motif identifiable in a protein sequence that has a predicted α helical conformation. Secondly, glycine residues which are frequently found in helix-turn-helix motif (1) as well as in two component signal transduction systems (14) are noticeably absent. Third, a small molecular size together with a high percentage of charged residues (33%) and a basic charge are molecular properties that are consistent with those found in other DNA binding proteins (21). Fourth, in contrast to the agr locus, direct sequence comparison of the sarA gene with prototypic sensor and activator genes in *E. coli*, *S. typhimurium* and *B. subtilis* did not reveal any significant similarity to two component regulatory systems (14). Finally, sequence similarity with virF, which is a positive regulator of invasive genes in a regulon carried on a large plasmid in *Shigella flexneri* (8,18), is of comparative interest. Like that of virF which regulates target genes via the control of another positive regulatory gene virB, the sarA gene may govern the expression of exoprotein genes (e.g., α and β hemolysins) by positively controlling the level of RNAIII. However, the exact mechanism by which the sarA gene production interacts with the agr locus is not apparent from the sequence analysis.

The postexponential regulation of exoprotein genes in *S. aureus* involves at least three global regulatory systems (sar, agr, and xpr). Although the evidence suggests that the sarA gene may control exoprotein synthesis via the control of agr, the relationship between sarA and xpr is not clear. Nevertheless, the observation that both agr and xpr mutants produce greatly reduced amounts of RNAIII transcript has led to the idea that agr and xpr loci may behave as interactive regulatory genes. It is therefore, conceivable that the sarA may interact with the xpr locus as well.

It should be noted, however, that the restoration of RNAIII transcript (FIG. 2) upon the introduction of the sarA gene in pALC4, was never complete. This raises the possibility that additional signals may be required for a normal pattern of RNAIII transcription, thereby leading to optimal expression of exoproteins at postexponential phase. Based on the pattern of transcription of an exoprotein gene such as hemolysin in an agr$^+$ parent, Vandenesch et al. suggested that a separate postexponential signal independent of agr may be needed for augmented α-hemolysin transcription during the postexponential phase (22).

The exact mechanism by which the sarA gene controls agr is not well understood. It is possible that the gene product of sarA binds to the promoter region of RNAIII.

BRIEF DESCRIPTION OF THE FIGURES

FIG. 2. Nucleotide sequence of the sarA gene (SEQ ID NO: 1). The ribosomal binding site is underlined. The arrow marks the site of transposon insertion. The protein sequence similarity between sarA and virF is also shown (SEQ ID NO: 2-5).

DESCRIPTION OF THE INVENTION

Figure 1A:
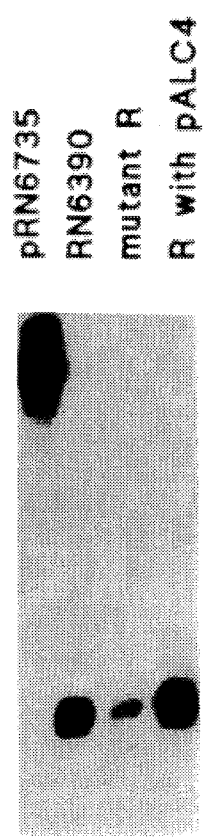
FIG. 1. Northern blots of RNAIII transcript in two sets of S. aureus strains. The first set (a) includes RN6390, mutant R and R complemented with pALC4 (carrying an intact sarA gene). The second set (b) comprises of RN450, mutant A and A complemented with pALC4. The plasmid pRN6735 is positive control and comprises of RNAIII cloned into pRN6725 (22).

A product of this invention is a regulatory protein of S. aureus which controls the expression of potential virulence factors such as bacterial enodotoxins. It has been designated sar for staphylococcal accessory regulator. It is useful for designing analogs which interfere with the expression of these toxins thereby, functioning as an antimicrobial agent to render the microorganism avirulent.

Through the use of the gene which expresses this protein or a fragment of said gene, a method is provided for the diagnostic identification of pathogenic staphylococci which express the protein and the resulting virulence factor. In this method, DNA is extracted from the microbial isolated suspected to be pathogenic and examined for complementary nucleotide sequences by hybridization to the molecular probe which may be labeled gene or a labeled segment thereof.

More specifically, the suspected staphylococcal isolate may be incubated with lysostaphin to digest the cell and release its DNA which is purified by any of the procedures known to the skilled artisan. The DNA is then contacted with the selected probe. Hybridization, detected by the selected label is a positive indication of the presence of the sar gene and that therefore, the strain of S. aureus isolated is capable of releasing toxic products.

The various methods employed herein are described below.

Bacterial strains, plasmids and phage

The bacterial strains and plasmids used in this study are listed in Table 1. Phage φ11 was used as a transducing phage for strains RN4220, RN450 and Rn6390(3). The following media were used for bacterial growth: CYGP broth for S. aureus 915), Luria-Bertani broth (LB) for E. coli (13). Antibiotics were used at the following concentrations: ampicillin at 50 µg/ml for E. coli, tetracycline at 5 µg/ml and erythromycin at 10 µg/ml for S. aureus. Carboxyphenylbenzoyl-aminopenicillanic acid (CBAP) (Sigma), an inducer of the β-lactamase promoter in pRN6735, was used at a concentration of 4 µg/ml.

Cloning and sequencing strategies

The transposon Tn917LTV1 inserted into the sar locus of the host chromosome contain an E. coli replicon carrying ampicillin as a selective marker (2). Taking advantage of the unique restriction sites (Xho and BalI) within the transposon, ligation mixture of sar mutant 11D2 (3) chromosomal DNA digest were transformed with one of these enzymes into E. coli strain HB101. Two plasmid clones (pALC1 and pALC2) comprised partly of transposon and adjacent staphylococcal chromosomal sequences were generated. (Table 1). The plasmid pALC1 was purified (13) and digested with XhoI/SalI to release a 4 kb flanking chromosomal fragment which as then cloned into pUC18 to form the pALC3. The 4 kb insert was subsequently released from pUC18 by digestion with SacI/SalI, gel-purified and labeled with $^{32}P$ ($\alpha$-$^{32}P$ deoxycytidine triphosphate, Amersham) (7) to probe a Zap genomic library (Stratagene, La Jolla, Calif.) of S. aureus strain DB as described in the manufacturer's instruction. Two pBluescript phagemids were obtained with inserts of 4.7 and 6 kb, respectively. Plasmids were purified by Magic Maxiprep (Promega, Madison, Wis.). Using both T3 and T7 primers, bidirectional plasmid sequencing was performed with $^{35}S$ sequencing mix and Sequenase (US Biochemicals) according to the chain termination method of Sanger (13,19). Additional primers were obtained for sequencing from within the insert. Based on the sequence generated, additional primers were also made to amplify the sar gene (designated sarA henceforth) from chromosomal DNA of prototypic S. aureus strains RN6390 and RN450 (15). The PCR fragment (732 bp) was cloned into pCRiI (Invitrogen, San Diego, Calif.), cleaved with XbaI/KpnI, and recloned into shuttle vector pSPT1818 (10) in E. coli strain XL-1 blue.

Evidence that sarA is necessary for the optimal expression of agr

Shuttle plasmid pSPT181 carrying the cloned sarA gene (designated pALC4) from strain RN6390 was transformed into RN4220 by protoplast transformation (3) to select for $Tc^r$ colonies at 32° C. A φ11 lysate of a RN4220 $Tc^r$ transformant, which has been verified to carry the reconstructed plasmid pALC4 by restriction analysis (3), was prepared and used to infect sar mutants R and A (derived from RN6390 and RN450, respectively) to obtain $Tc^r$ $ERm^r$ transductants. Positive transductants were verified by restriction analysis.

To verify that the cloned sarA gene is responsible for the production of selected hemolysins in the complemented sar mutants, for α, β and δ hemolysin production was essayed on plain and cross streaked sheep and rabbit erythrocyte agar using specific indicator strains as standards as previously described (17). This confirmed the restoration of α- and β-hemolysin production in mutants R and A, respectively, upon the introduction of the plasmid pALC4 (Table 2). Using the culture supernatants of RN6390 and mutant R as the respective positive and negative controls, verified the secretion of hemolysin in complemented mutant R by probing the culture supernatant of this strain with affinity-purified anti-α hemolysin antibody in an immunoblot as previously described (4).

To evaluate the effect of a sar mutation on RNAIII (the agr regulatory molecule), bacterial RNA was prepared from two pairs of isogenic S. aureus strains (RN450 and RN6390 together with their sar mutants) and their corresponding complemented mutants using a method described by Kornblum et al. (12). For Northern blots, equal volumes (≈7.5 µl) of samples extracted from equivalent number of bacterial cells at late log phase were electrophoresed through a 1.5% agarose-0.66M formaldehyde gel in MOPS running buffer (20 mM MOPS, 10 mM sodium acetate, 2 mM EDTA, pH 7.0) (13). RNA was transferred onto Hybond N membrane (Amersham) according to manufacture's instruction and allowed to hybridize in 50% formamide at 42° C. overnight with a $^{32}P$ labeled (random-primed) gel-purified RNAIII probes (1.5 kb MboI fragment of pRN6735—Table 1) (13). Following hybridization, the membrane was washed twice in 2x SSC with 0.1% SDS at RT for 10 min. each, once with 1x SSC with 0.1% SDS at 55° C. for 15 min, and finally autoradiographed.

Figure 1B:
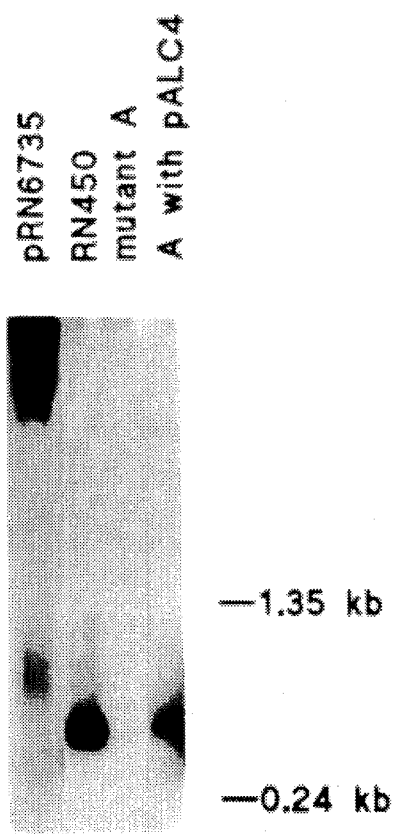

As shown in FIG. 1A and 1B, the levels of RNAIII in mutants A and R were neither absent or significantly diminished as compared to the parents. However, mutants A and R transformed with the shuttle plasmid, pALC4, which carried an intact sarA probe, were able to partially restore RNAIII levels to that of the parents (FIG. 1A and 1B).

If sarA is assumed to be a positive regulator of agr, one would expect complementation of selected sar phenotypes with a plasmid carrying RNAIII (i.e., pRN6735 —see Table 1). As the cloned RNAIII fragment in pRN6735 was under the control of aβ-lactamase promoter that was normally repressed in the presence of pI524 (22), the production of RNAIII in mutant A was low at the basal level but was highly inducible by the addition of aβ-lactam compound such as carboxyphenylbenzoyl-aminopenicillanic acid (CBAP). Using this approach, it was found that the production of β hemolysin in the complemented mutant A35 was reestablished as compared with sar mutant A. Similarly, the production of hemolysin which was not detected in mutant A was weakly expressed in the complemented mutant (Table 2).

Sequence analysis of sarA gene

Using a 732 bp cloned sarA gene as a probe, Southern blot hybridization of chromosomal DNA digested with EcoRI (internal to the structural gene), HindIII and EcoRV (external to sarA) revealed one copy of this gene in three *S. aureus* strains, DB, RN450 and RN6390. Of these, the complete sarA gene of strains DB ad RN450 was sequenced. Sequence analysis and comparisons with known databases were conducted with the Sequence Analysis Software Package for the Genetics Computer Group (GcG package, University of Wisconsin, Madison, Wis.) (5). Sequence data revealed identical sarA sequences between the two strains. By sequencing plasmids (pALC2 and pALC3) comprised partly of transposon and flanking chromosomal sequences, site of the transposon Tn917LTV1 was located to 5 bp downstream from the translation start in strain DB (FIG. 2). The sarA gene has an open reading frame of 372 bp. The sequence has a GC content (27%) similar that found in the staphylococcal genome (30%) (6). A putative ribosomal binding site (underlined) is indicated in FIG. 2. The mature protein has a predicted molecular size of 14,718 Da with a deduced basic pI of 8.52. The deduced protein has a predominance of charges residues (33%). Four major residues constitute ≈44% of its composition -lysine 12.9%), glutamic acid (11.2%), leucine (10.4%) and isoleucine (9.6%). In addition, there is an absence of glycine and tryptophan residues. Garnier analysis of the deduced amino acid sequence suggested that the molecule is primarily α helical (77%) (5). Additional conformational analysis with the GCG package indicated that a helix-turn-helix motif is not apparent in the deduced sequence. It also does not appear to have significant similarity with sequence elements of the two-component signal transduction system that are located in the CX-terminal domain of the signaling component and in the N-terminal domain of the activator component (14). Comparison of this protein sequence with others in the Genbank database revealed similarity to virF gene of *Shigella flexneri* (18) (FIG. 2).

TABLE 1

Bacteria strains and plasmids

| Types | Ref. | Comments |
|---|---|---|
| A) Bacterial strains | | |
| *S. aureus* | | |
| DB | (3) | A wild type blood isolate |
| RN450 | (15) | A prototypic strain, which is a derivative of NTCC 8325 cured of prophage, secretes β but not α hemolysin |
| RN6390 | (15) | A laboratory strain that maintains its hemolytics pattern when propagated on sheep red blood cells |
| RN4220 | (15) | A mutant of strain 8325-4 that accepts foreign DNA |
| 11D2 | (3) | A mutant derived of DB with a sar::Tn917LTV1 mutation |
| A | this disclosure | An isogenic mutant of RN450 with a sar::Tn917LTV1 mutation |
| R | this disclosure | An isogenic mutant of Rn6390 carrying a sar::Tn917LTV1 mutation |
| RN7372 | (22) | A derivative of RN6911 (Tc$^r$) containing pRN6735 and pI524 |
| A35 | this disclosure | A derivative of mutant A (Tc$^r$) carrying two plasmids, pRN6735 and pI524 |
| C7 | this disclosure | A derivative of mutant R (Tc$^r$) containing pRN6735 and pI524 |
| *E. coli* | | |
| HB101 | (13) | A highly transformable strain |
| B) Plasmids | | |
| pALC1 | this disclosure | An *E. coli* plasmid comprising partly of transposon Tn917LTV1 and flanking sar sequence (near the erm-proximal end) was generated by ligating XhoI mutant 11D2 |
| pALC2 | this disclosure | An *E. coli* plasmid generated by ligating BalI digests of 11D2 - this contains flanking sar sequence distal to the erm-proximal end of the transposon |
| pALC3 | this disclosure | pUC18 with a 4 kb chromosomal insert from pALC1 |
| pSPT181 | (10) | A shuttle vector |
| pCRII | | A vector for cloning PCR fragment |
| pALC4 | this disclosure | pSPT181 containing a 732 bp PCR fragment of sarA gene of RN6390 |
| pI524 | (22) | A 30 kb *S. aureus* plasmid encoding the β-lactamase repressor |
| pRN6735 | (22) | A derivative of pC194 |

TABLE 1-continued

Bacteria strains and plasmids

| Types | Ref. | Comments |
|---|---|---|
| | | (15) containing pI258bla promoter and ⅔ of the blaZ gene followed by the 1,566 bp MboI fragment of RNAIII lacking its promoter |

TABLE 2

Complementation of α and β hemolysin expression in sar mutants

| Starins | α hemolysin | β hemolysin | hemolysin |
|---|---|---|---|
| RN450 | − | ++ | +/− |
| A | − | − | − |
| A with pALC4 | − | ++ | +/− |
| A35 (no CBAP) | − | + | − |
| A35 (CBAP) | − | ++ | +/− |
| RN390 | + | ++ | + |
| R | − | − | − |
| R with pALC4 | + | ++ | ++ |

REFERENCES

1. Brennan, R. G. and B. W. Matthews. 1989 the helix-turn-helix binding motif. J. Biol. Chem. 264:1903–1906.
2. Camilli, A., D. A. Portnoy, and P. Youngman. 1990 Insertional mutagenesis of *Listeria monocytogenes* with a novel Tn917 derivative that allows direct cloning of DNA flanking transposon insertions. J. Bacteriol. 172:3738–3744.
3. Cheung, A. L., J. M. Koomey, C/A/Butler, S. J. Projan, and V. A. Fischetti. 1992. Regulation of exoprotein expression in *Staphylococcus aureus* by a locus (sar) distinct from agr. Proc. Natl. Acad. Sci. USA. 89:6462–6466.
4. Cheung, A. L. and P. Ying. 1994. Regulation of and hemolysins by the sar locus of *S. aureus*. J. Bacteriol. 176:580–585.
5. Devereux, J., P. Haeberli, and O. Smithies. 1984. A comprehensive set of analysis programs for the VAX. Nucl. Acids Res. 12:387–395.
6. Easmon, C. S. F. and C. Adlam. 1983. Staphylococci and staphylococcal infections, Academic Press, New York.
7. Feinberg, A. P. and B. Vogelstein. 1983. A technique for radiolabeling DNA restriction endonuclease fragments to high specific activity. Anal. Biochem. 132:6–13.
8. Hale, T. L. 1991. Genetic basis of virulence in Shigella species. Microbiol. Rev. 55:206–224.
9. Hart, M. E., M. S. Smeltzer, and J. J. Iandolo. 1993. The extracellular protein regulator (xpr) affects exoprotein and agr mRNA levels in *Staphylococcus aureus*. J. Bacteriol. 175:7875–7879.
10. Janzon, L. and S. Arvidson. 1990. The role of the -heolysin gene (hld) in the regulation of virulence genes by the accessory gene regulator (agr) in *Staphylococcus aureus*. EMBO. J. 9:1391–1399.
11. Kornblum, J., B. Kreiswirth, S. J. Projan, H. Ross, and R. P. Novick. 1990. Agr: A polycistronic locus regulating exoprotein synthesis in *Staphylococcus aureus*, p.373–402. In R. P. Novick (ed.), Molecular biology of the staphylococci, VCH Publishers, New York.
12. Kornblum, J., S. J. Projan, S. L. Moghazeh, and R. Novick, 1988. A rapid method to quantitate non-labeled RNA species in bacterial cells. Gene 63:75–85.
13. Maniatis, T., E. F. Fritsch, and J. Sambrook. 1989. Molecular cloning,a laboratory manual, cold Spring Harbor Laboratory, Cold Spring Harbor, NY.
14. Nixon, B. T., C. W. Ronson, and R. M. Ausubel. 1986. Two component regulatory systems responsive to environmental stimuli share strongly conserved domains with the nitrogen assimilation regulatory genes ntrB and btrC. Proc. Natl. Acad. Sci. USA. 83:7850–7854.
15. Novick, R. P. 1991. Genetic systems in staphylococci. Methods Enzymol. 204:587–636.
16. Novick, R. P., H. F. Ross, S. J. Projan, J. Kornblum, B. Kreiswirth, and S. Moghazeh. 1993. Synthesis of staphylococcal virulence factors is controlled by a regulatory RNA molecule. EMBO. J. 12:3967–3977.
17. Rescei, P., B. Kreiswirth, M. O'Reilly, P. Schlievert, A. Gruss, and R. P. Novick. 1986. Regulation of exoprotein gene expression in *Staphylococcus aureus* by agr. Mol. Gen. Genet.202:58–61.
18. Sakai, T., C. Sasakawa, S. Makino, and M. Yoshikawa. 1986. DNA sequence and product analysis of the virF locus responsible for congo red binding and cell invasion in *Shigella flexneri* 2a. Infect. Immun. 54:395–402.
19. Sanger, F., S. Nicklen, and A. R. Coulson. 1977. DNA sequencing with chain terminating inhibitors. Proc. Natl. Acad. Sci. USA. 74:5463.
20. Smeltzer, H. S., M. E. Hart, and J. J. Iandolo. 1993. Phenotypic characterization of xpr, aglobal regulator of extracellular virulence factors in *Staphylococcus aureus*. Infect. Immun. 61:919–925.
21. Smith, I. 1993. Regulatory proteins that control late-growth development, p.785–800. In A. L. Sonenshein, J. A. Hoch, and R. Losick (ed.), *Bacillus subtilis* and other gram positive bacteria, ASM Press, Washington D.C.
22. Vandenesch, F., J. Kornblum, and R. P. Novick. 1991. A temporal signal, independent of agr, is required for hla but not spa transcription in *staphylococcus aureus*. J. Bacteriol. 173:6313–6320.

All of the above references are incorporated by reference herein.

What is claimed is:

1. An isolated, purified *S. aureus* staphylococcal accessory regulatory (sar) protein, consisting of the amino acid sequence shown in SEQ ID NO. 1.

2. An isolated, purified *S. aureus* gene sar comprising a contiguous nucleotide sequence encoding the sar protein of claim 1.

3. A sar gene according to claim 1, wherein the gene consists of the nucleotide sequence of SEQ ID NO. 1.

* * * * *

UNITED STATES PATENT AND TRADEMARK OFFICE
CERTIFICATE OF CORRECTION

PATENT NO. : 5,587,288
DATED : Dec. 24, 1996
INVENTOR(S) : Cheung et al.

It is certified that error appears in the above-indentified patent and that said Letters Patent is hereby corrected as shown below:

Claim 3, column 12, line 40, "1" should be --2--, and "gone" should be --gene--.

Signed and Sealed this

Sixth Day of May, 1997

Attest:

BRUCE LEHMAN

*Attesting Officer*  *Commissioner of Patents and Trademarks*